United States Patent
Wilson et al.

(10) Patent No.: US 9,880,384 B2
(45) Date of Patent: Jan. 30, 2018

(54) GAZE DETECTION SYSTEM, GAZE POINT DETECTION METHOD, AND GAZE POINT DETECTION PROGRAM

(71) Applicant: FOVE, Inc., Tokyo (JP)

(72) Inventors: Lochlainn Wilson, Tokyo (JP); Keiichi Seko, Tokyo (JP); Yuka Kojima, Tokyo (JP); Yamato Kaneko, Tokyo (JP)

(73) Assignee: FOVE, Inc. (JP)

( * ) Notice: Subject to any disclaimer, the term of this patent is extended or adjusted under 35 U.S.C. 154(b) by 0 days.

(21) Appl. No.: 15/318,709

(22) PCT Filed: Nov. 27, 2015

(86) PCT No.: PCT/JP2015/083484
§ 371 (c)(1),
(2) Date: Dec. 14, 2016

(87) PCT Pub. No.: WO2017/090203
PCT Pub. Date: Jun. 1, 2017

(65) Prior Publication Data
US 2017/0285337 A1    Oct. 5, 2017

(51) Int. Cl.
*G02B 27/00*    (2006.01)
*G02B 27/01*    (2006.01)

(52) U.S. Cl.
CPC ......... *G02B 27/0093* (2013.01); *G02B 27/00* (2013.01); *G02B 27/0012* (2013.01);
(Continued)

(58) Field of Classification Search
CPC ...... G02B 27/00; G02B 27/01; G02B 27/017; G02B 27/0012; G02B 27/0075; G02B 27/0093; G02B 2027/0187
(Continued)

(56) References Cited

U.S. PATENT DOCUMENTS 6,246,779 B1 *  6/2001  Fukui ................. G06K 9/00268
                                                    382/100
6,806,898 B1 * 10/2004  Toyama ................. G06T 5/006
                                                    348/14.01
(Continued)

FOREIGN PATENT DOCUMENTS

JP    2-264632 A    10/1990
JP    6-337756 A    12/1994
(Continued)

*Primary Examiner* — William R Alexander
(74) *Attorney, Agent, or Firm* — DLA Piper LLP (US)

(57) ABSTRACT

A gaze detection system includes a head mounted display and a gaze detection device detecting the gaze of the user. The head mounted display illuminate users eyes with infrared light, displays three-dimensional image comprising a plurality of layers in the depth direction and captures an image of user's eye illuminated by the infrared light. The gaze detection device detects the user's right eye's gaze direction (vector) and left eye's gaze direction (vector) with use of the captured images. The gaze detection device identifies the layer that the user is gazing at by selecting the layer having the shortest distance between the intersection points of the right eye gaze vector and the left eye gaze vector with each layer as a gaze point in the depth direction.

6 Claims, 12 Drawing Sheets

(52) U.S. Cl.
CPC ......... *G02B 27/0075* (2013.01); *G02B 27/01* (2013.01); *G02B 27/017* (2013.01); *G02B 2027/014* (2013.01); *G02B 2027/0187* (2013.01)

(58) Field of Classification Search
USPC .......................................................... 359/630
See application file for complete search history.

(56) References Cited

U.S. PATENT DOCUMENTS

| | | | | |
|---|---|---|---|---|
| 2013/0050258 | A1* | 2/2013 | Liu .................... | G06F 3/005 345/633 |
| 2015/0003819 | A1* | 1/2015 | Ackerman ............. | G02B 7/287 396/51 |
| 2015/0192992 | A1 | 7/2015 | DiCenso et al. | |
| 2015/0288944 | A1 | 10/2015 | Nistico et al. | |
| 2016/0085301 | A1* | 3/2016 | Lopez .................... | G06F 3/013 345/156 |
| 2016/0259977 | A1* | 9/2016 | Asbun .................... | A61B 5/165 |

FOREIGN PATENT DOCUMENTS

| | | |
|---|---|---|
| JP | 2015-130173 A | 7/2015 |
| WO | 2014/033306 A1 | 3/2014 |

* cited by examiner

US 9,880,384 B2

GAZE DETECTION SYSTEM, GAZE POINT DETECTION METHOD, AND GAZE POINT DETECTION PROGRAM

TECHNICAL FIELD

This disclosure relates to a head mounted display.

BACKGROUND

Technology exists for illuminating a user's eye with infrared or other non-visible light and detecting the gaze direction by analyzing images of light reflected from the user's eye in Japanese Patent Application No. H02-264632. The eye-gaze detection technique is known as analyzing the captured emitted light images of user's eye using illuminating light on the user's eye. The detected eye-gaze information can be used, for example, for PC (Personal Computer) or game monitoring, and can be applied to use as a pointing device.

The head mounted display is wearable on the user to display 3D images but normally covers the user's eye sights. The user therefore cannot recognize the outside environment while the user wears the HMD. If the user needs to find input devices such as a controller while wearing the HMD as a display device for movie or games, the user has difficulties to find controllers.

It could therefore be helpful to detect the user's eye-gaze direction to use as a substitute of pointing device while the user wears the HMD. Thus, it could be helpful to provide a technique that detects the gaze direction of a user wearing a head mounted display.

We provide a gaze detection system comprising: a head mounted display, mounted on a user's head for use, comprising, a first infrared light source unit illuminating the user's right eye with infrared light; a second infrared light source unit illuminating the user's left eye; a first image capturing device imaging the right eye illuminated by the infrared light source; a second image capturing device imaging the left eye illuminated by the infrared light source; and a display unit displaying a three-dimensional image, and a gaze detection device, detecting the gaze of the user, comprising, a first detection unit detecting the gaze direction of the right eye, based on the image captured by the first image capturing device; a second detection unit detecting the gaze direction of the left eye, based on the image captured by the second image capturing device; and a tracking unit determining the gaze point of the user in the three-dimensional image on the basis of the gaze direction of the right eye and the gaze direction of the left eye.

Also, the first detection unit may calculate the right eye gaze vector indicating the gaze direction of the right eye, and the second detection unit may calculate the left eye gaze vector indicating the gaze direction of the left eye.

The display unit may display a three-dimensional image consisting of a plurality of layers in the depth direction, and the tracking unit may identify the layer that the user is gazing at by selecting the layer having the shortest distance between the intersection points of the right eye gaze vector and the left eye gaze vector with each layer.

The tracking unit may identify the user's gaze location based on the intersection point between the right eye gaze vector and the left eye gaze vector.

The tracking unit may identify the user's gaze location based on the intersection region of a cylinder with a given radius, centered on the right eye gaze vector and a cylinder with a given radius, centered on the right eye gaze vector.

The tracking unit may identify the gaze location of the user based on the intersection points of the first plurality of parallel vectors parallel to the right eye gaze vector and the second plurality of parallel vectors parallel to the left eye gaze vector.

Additionally, any combination of the aforementioned components, and the implementation in the form of methods, devices, systems, computer programs, data structures, recording mediums, and the like may be effective.

We thus disclose a technique to detect the gaze direction of a user wearing a head mounted display.

REFERENCE LIST

1: gaze detection system, 100: head mounted display, 103a: infrared light source (second infrared light illumination unit), 103b: infrared light source (first infrared light illumination unit), 105: bright spot, 108: image display element, 112: hot mirror, 114, 114a, 114b: convex lens, 116: camera (first imaging unit, second imaging unit), 118: first communication unit, 121: display unit, 122: infrared illumination unit, 123: image processing unit, 124: image capturing unit, 130: image display system, 150: housing, 152a, 152b: lens holder, 160: fitting harness, 170: headphone, 200: gaze detection device, 220: second communication unit, 221: first gaze detection unit, 222: second gaze detection unit, 223: tracking unit, 224: video output unit, 225: storage unit

DETAILED DESCRIPTION

Figure 1:
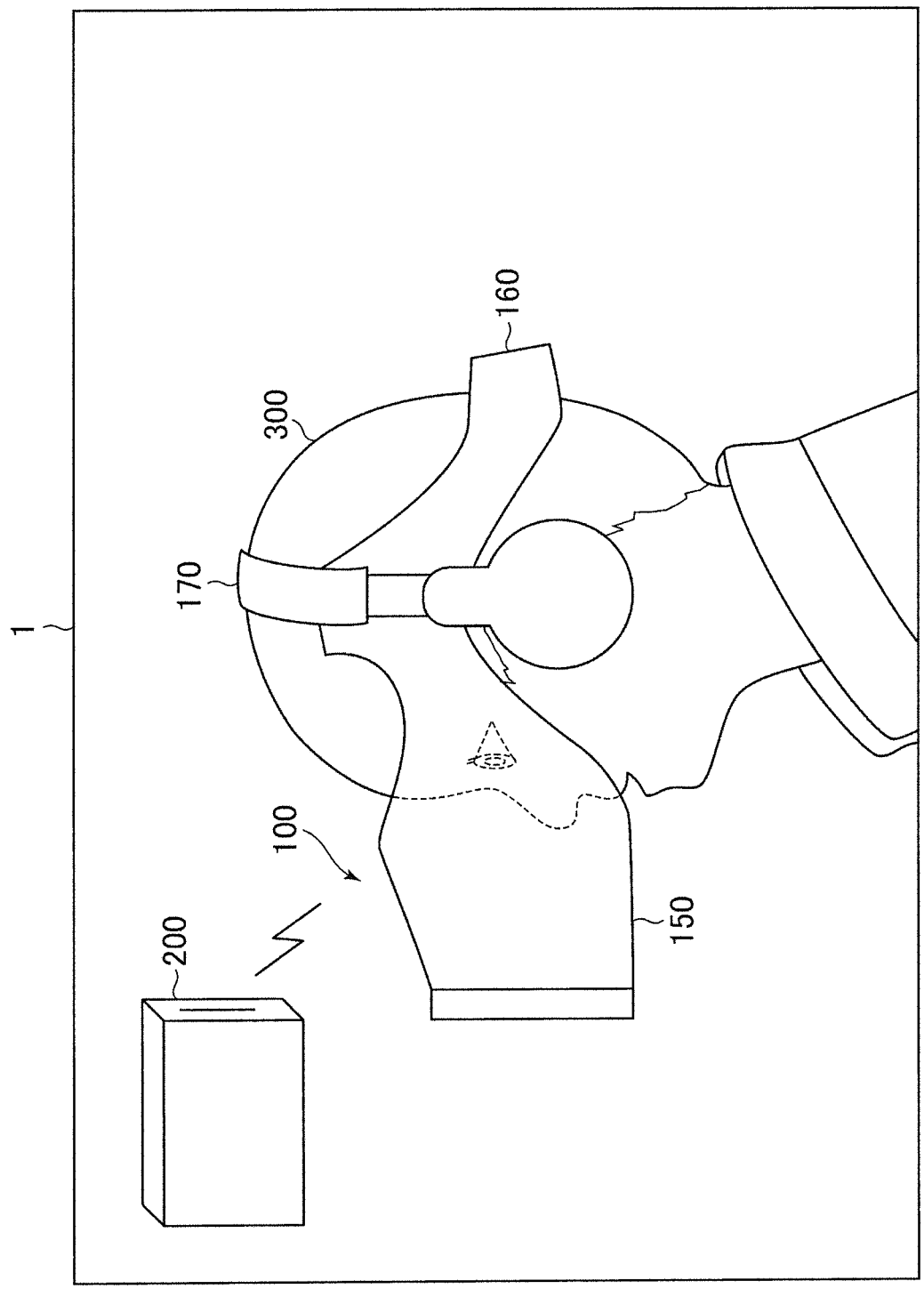
FIG. 1 is an external view illustrating the head mounted display worn by a user.

FIG. 1 shows a typical view of the gaze detection system 1 as described in the examples. The gaze detection system 1 comprises a head mounted display 100 and a gaze detection device 200. As shown in FIG. 1, the head mounted display 100 is mounted on the head of the user 300 for use.

The gaze detection device 200 measures the gaze direction and the focal point of the right and left eyes of the user wearing the head mounted display 100, determining the gaze point of the user in the three-dimensional image displayed by the head mounted display. The gaze detection device 200 also functions as a video generator device to create the video images displayed on the head mounted display 100. For example, the gaze detection device 200 can be used to reproduce video images on stationary game machines, portable game machines, PCs, tablets, smartphones, phablets, video players, TVs and the like. The gaze detection device 200 establishes a wireless or a wired connection with the head mounted display 100. In the example shown in FIG. 1, the gaze detection device 200 wirelessly connects to the head mounted display 100. The wireless connection between the gaze detection device 200 and the head mounted display 100 may be established using existing wireless communication techniques such as Wi-Fi (registered trademark) or Bluetooth (registered trademark). Without being limited to these two methods, video image transfer between the head mounted display 100 and the gaze detection device 200 may be implemented using, for example, Miracast (registered trademark), WiGig (registered trademark), WHDI (registered trademark) or other communication standards.

It should be noted that the example in FIG. 1 illustrates that the head mounted display 100 and the gaze detection device 200 are separate units. However, the gaze detection device 200 may also be incorporated into the head mounted display 100.

The head mounted display 100 includes a housing 150, a fitting harness 160, and headphones 170. The housing 150 contains an image display system for displaying video images to the user 300, and, not shown in the figure, a communications module using Wi-Fi (registered trademark), Bluetooth (registered trademark), or other wireless technology. The head mounted display 100 is secured to the head of the user 300 with a fitting harness 160. The fitting harness 160 may be implemented with the help of, for example, belts or elastic bands. When the user 300 wears the head mounted display 100, the fitting harness 160 holds the housing 150 in a position where the eyes of the user 300 are covered. Thus, once the user 300 wears the head mounted display 100, the field of view of the user 300 is covered by the housing 150.

The headphones 170 output the audio of the video reproduced by the gaze detection device 200. The headphones 170 do not need to be fixed to the head mounted display 100. Even if the head mounted display 100 is equipped with a fitting harness 160, the user 300 may freely attach or detach the headphones 170.

Figure 2:
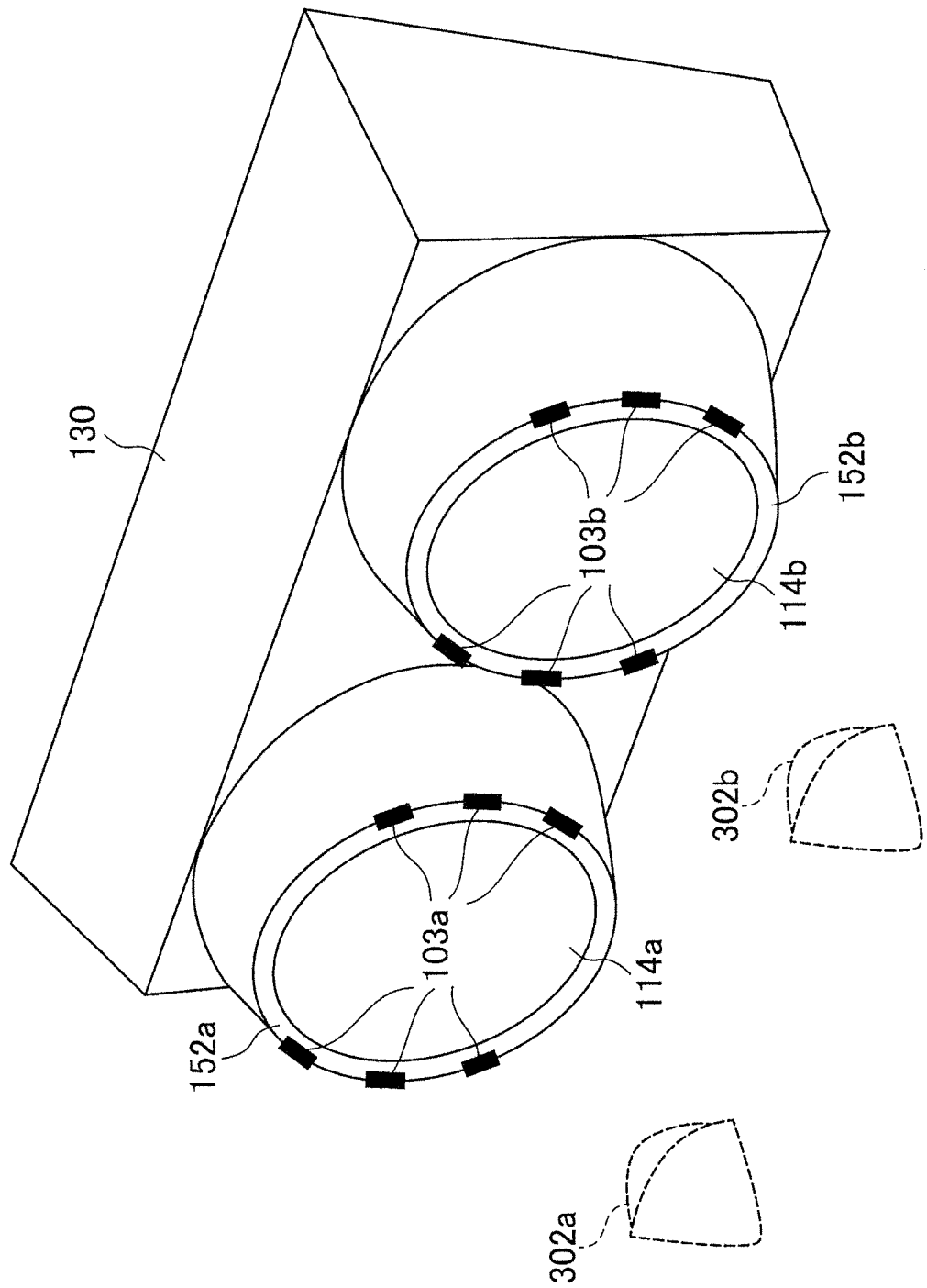
FIG. 2 is a perspective overview of the image display system of the head mounted display.

FIG. 2 is a perspective diagram showing the overview of the image display system 130 of the head mounted display 100 described in the examples. Specifically, FIG. 2 shows the part of the housing 150 facing the corneas 302 when the user 300 is wearing the head mounted display 100.

As shown in FIG. 2, a convex lens 114a is positioned to face the cornea 302a of the left eye of the user 300 when the user 300 wears the head mounted display 100. Similarly, a convex lens 114b is positioned to face the cornea 302b of the right eye of the user 300 when the user 300 wears the head mounted display 100. The convex lens 114a for the left eye and the convex lens 114b for the right eye are held by a lens holder 152a for the left eye and a lens holder 152b for the right eye, respectively.

Hereinafter, the convex lens 114a for the left eye and the convex lens 114b for the right eye are referred to as a "convex lens 114" unless the two lenses need to be specifically distinguished. Likewise, the cornea 302a of the left eye of the user 300 and the cornea 302b of the right eye of the user 300 are simply referred to as a "cornea 302" unless the corneas need to be specifically distinguished. The lens holder 152a for the left eye and the lens holder 152b for the right eye are referred to as a "lens holder 152" unless the holders need to be specifically distinguished.

Multiple infrared light sources 103 are attached to the lens holders 152. For the purpose of brevity, in FIG. 2, the infrared light sources illuminating cornea 302a of the left eye of the user 300 with infrared light are collectively referred to as infrared light sources 103a, and the infrared light sources illuminating the cornea 302b of the right eye of the user 300 with infrared light are collectively referred to as infrared light sources 103b. Hereinafter, the infrared light sources 103a and the infrared light sources 103b are collectively referred to as "infrared light sources 103" except when a distinction between the two is necessary. In the example shown in FIG. 2, six infrared light sources 103a are attached to the lens holder 152a for the left eye. In the same manner, six infrared light sources 103b are attached to the lens holder 152b for the right eye. In this way, the infrared light sources 103 are not attached directly to the convex lenses 114, but are mounted on the lens holders 152 that grip the convex lenses 114, making the attachment of the infrared light sources 103 easier. Since the lens holders 152 are typically made of a resin or the like, machining that is necessary to attach the infrared light sources 103 is easier than for the convex lenses 114 that are made of glass or the like.

As mentioned above, the lens holders 152 is a component that holds the convex lenses 114. Therefore, the infrared light sources 103 mounted on the lens holders 152 are positioned along the circumference of the convex lenses 114. Although six infrared light sources 103 illuminating each eye with infrared light are shown here, the number of the infrared light sources 103 is not limited to this number, there should be at least one light source 103 for each eye, and two or more light sources 103 are desirable.

Figure 3:
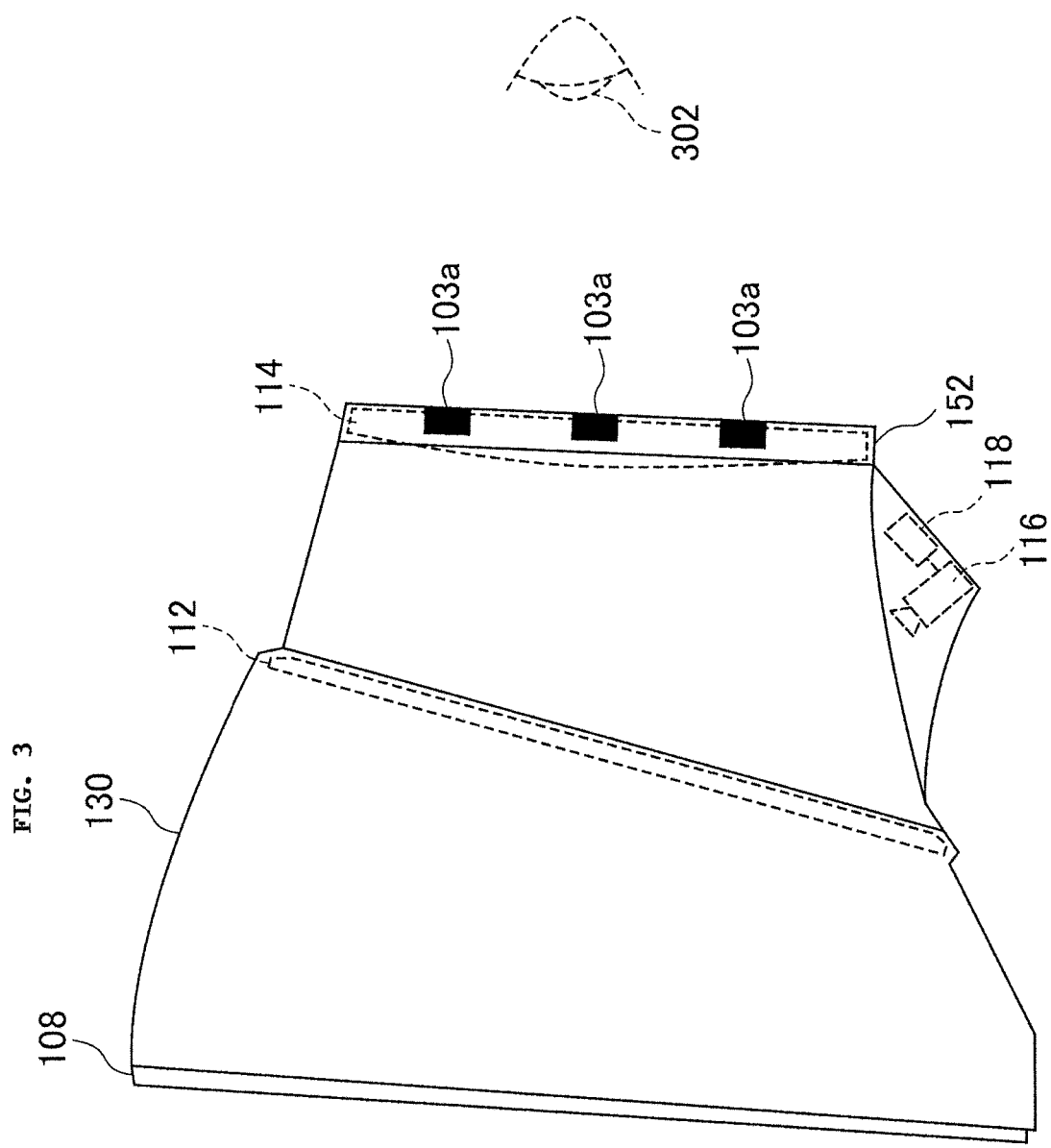
FIG. 3 is a diagram schematically illustrating the optical configuration of the image display system of the head mounted display.

FIG. 3 is a schematic diagram of the optical configuration of the image display system 130 contained in the housing 150 according to the example, with the diagram showing a view of the housing 150 from the direction of the left eye as shown in FIG. 2. The image display system 130 includes infrared light sources 103, an image display element 108, a hot mirror 112, the convex lenses 114, a camera 116, and a first communication unit 118.

The infrared right sources 103 are light sources capable of near-infrared light (700 nm to 2500 nm range). Near-infrared light is a type of non-visible light in a wavelength region that cannot be detected by the naked eye of the user 300.

The image display element 108 displays an image to be presented to the user 300. The image displayed by the image display element 108 is generated by a video output unit 224 in the gaze detection device 200. The video output unit 224 will be described later. The image display element 108 may be implemented by using existing liquid crystal display (LCD), or organic EL display (Organic Electro Luminescence Display).

The hot mirror 112 is positioned between the image display element 108 and the cornea 302 of the user 300 when the user 300 wears the head mounted display 100. The hot mirror 112 has a property of transmitting visible light created by the image display element 108 and reflecting near-infrared light.

The convex lenses 114 are positioned on the opposite side of the hot mirror 112 from the image display element 108. In other words, the convex lenses 114 are positioned between the hot mirror 112 and the cornea 302 of the user 300 when the user 300 wears the head mounted display 100. That is, the convex lenses 114 are positioned to face the corneas 302 of the user 300 when the user 300 wears the head mounted display 100.

The convex lenses 114 condenses the light from the image display transmitted through the hot mirror 112. Thus, the convex lenses 114 function as image magnifiers that enlarge an image created by the image display element 108 and presented to the user 300. Although only one convex lens 114 is shown in FIG. 2 for convenience, instead of a single convex lens 114, a lens group may be used that combines various kinds of lenses, including plano-convex lenses and biconvex lenses.

A plurality of infrared light sources 103 are arranged along the circumference of the convex lens 114. The infrared light sources 103 emit infrared light toward the cornea 302 of the user 300.

Although not shown in the figure, the image display system 130 of the head mounted display 100, according to the example, contains two image display units 108, where the image presented to the right eye of the user 300 and the image presented to the left eye of the user can be independently generated. Accordingly, the head mounted display 100, according to the example may present to the right and left eyes of the user 300, respectively a parallax image for the right eye and a parallax image for the left eye. Thereby, the head mounted display 100, according to the example, can present a stereoscopic scene that creates a feeling of depth for the user 300.

As mentioned above, the hot mirror 112 transmits visible light but reflects the near-infrared light. Thus, the image light emitted by the image display element 108 is transmitted through the hot mirror 112, and reaches the cornea 302 of the user 300. The infrared light emitted from the infrared light sources 103 and internally reflected in the reflective area of the convex lens 114 reaches the cornea 302 of the user 300.

The infrared light reaching the cornea 302 of the user 300 is reflected on the cornea 302 of the user 300 and directed again towards the convex lens 114. The infrared light reflected by the cornea of the user is transmitted through the convex lens 114 and reflected by the hot mirror 112. The camera 116 includes a filter that blocks the visible light, and the near-infrared light reflected from the hot mirror 112 is used for imaging. That is, the camera 116 is a near-infrared camera that images the near-infrared light emitted from the infrared light sources 103 and reflected on the cornea of the eye of the user 300.

Although not shown in the figure, the image display system 130 of the head mounted display 100, according to the example, includes two cameras 116, that is, a first image capturing unit that captures an image containing the infrared light reflected from the right eye and a second image capturing unit that captures an image containing the infrared light reflected from the left eye. Thereby, images used to detect gaze directions of both the right eye and the left eye of the user 300 can be acquired.

The first communication unit 118 outputs the image captured by the camera 116 to the gaze detection device 200 that determines the gaze direction of the user 300. Specifically, the first communication unit 118 transmits the image captured by the camera 116 to the gaze detection device 200. Although a detailed description of the first detection unit 221 and the second detection unit 222 that functions as a gaze (direction) detection unit will be given later, the gaze direction is determined with the help of a gaze detection program executed by the by CPU (Central Processing Unit) of the gaze detection device 200. When the head mounted display 100 has the necessary computational resources such as a CPU, memory or the like, the CPU of the head mounted display 100 may execute the program to determine the gaze direction.

Although a detailed description will be given later, the image captured by the camera 116 contains bright spots caused by the near-infrared light reflected from the cornea 302 of the user 300 and an image of the eye including the cornea 302 of the user 300 observed in the near-infrared wavelength region.

Although the aforementioned description has been given mainly for the configuration of presenting an image to the left eye of the user 300 in the image display system 130, according to the example, the configuration that presents an image to the right eye of the user 300 is the same.

Figure 4:
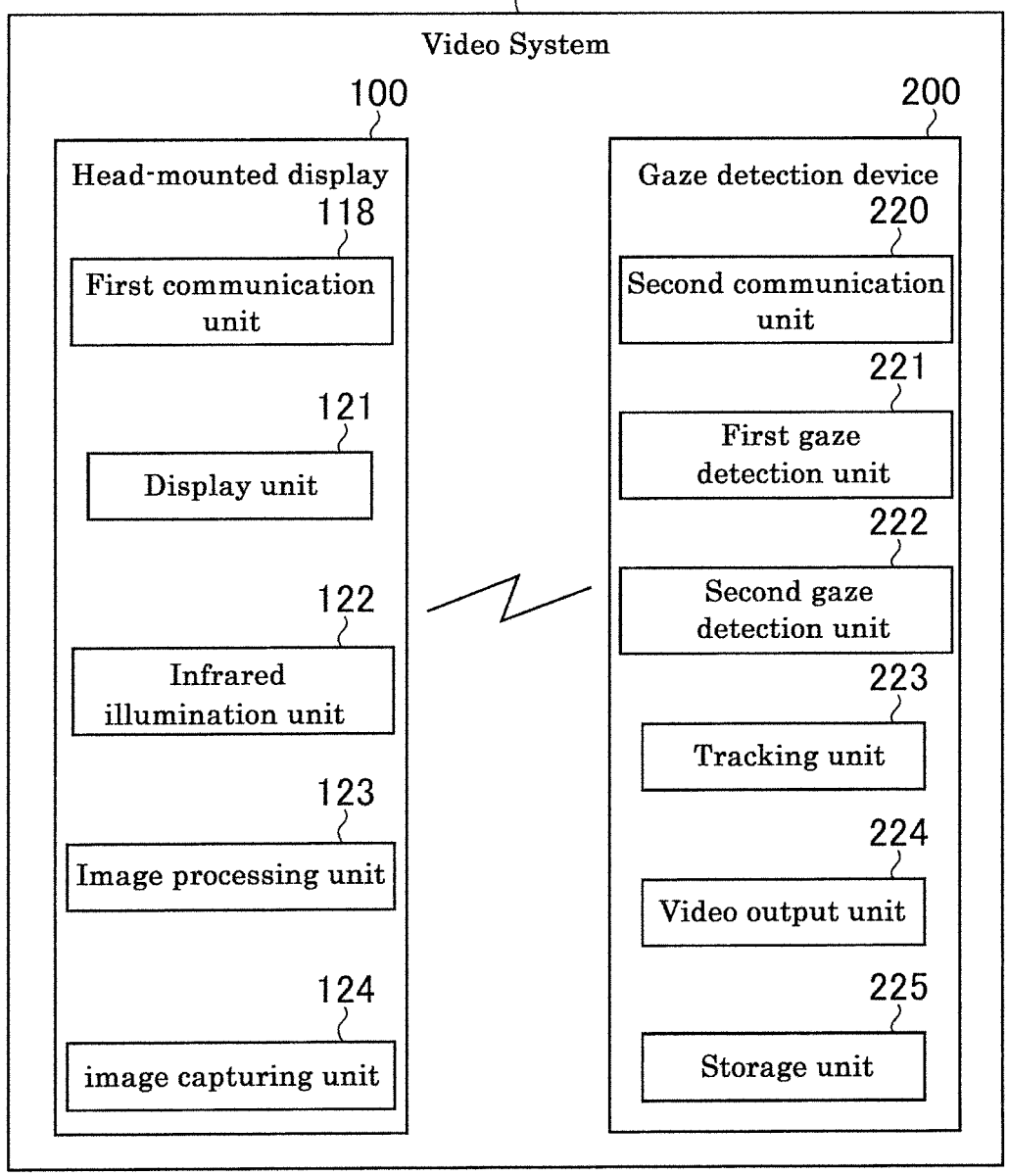
FIG. 4 is a block diagram illustrating the components of the head mounted display.

FIG. 4 is a block diagram of the head mounted display 100 and the gaze detection device 200 contained in the gaze detection system 1. As shown in FIG. 4, and as explained above, the gaze detection system 1 contains the head mounted display 100 and the gaze detection device 200, both of which communicate with each other.

As shown in FIG. 4, the head mounted display 100 contains the first communication unit 118, the display unit 121, the infrared illumination unit 122, the image processing unit 123, and the image acquisition unit 124.

The first communication unit 118 is a communication interface having the capability to communicate with the second communications unit 220 contained inside the gaze detection device 200. As mentioned above, the first communication unit 118 communicates with the second communication unit 220 over a wired or wireless communication link. Examples of possible communication standards were already given above. The first communication unit 118 transmits image data to be used for gaze detection, obtained from either the image acquisition unit 116 or the image processing unit 123, to the second communication unit 220. Further, the first communication unit 118 delivers to the display unit 121 three-dimensional image data sent from the gaze detection device 200.

The function of the display controller 121 is to display on the image display unit 121 the three-dimensional image based on the three dimensional image data sent from the first communication unit 118. The three-dimensional image data represents a parallax image pair containing a parallax image for the right eye and a parallax image for the left eye.

The infrared illumination unit 122 controls the infrared light sources 103 and illumination of the user's right eye or the left eye with infrared light.

The image processing unit 123 performs image processing of the image data acquired by the image acquisition unit 116 as necessary, and passes the processed data to the first data communication unit 118.

The image capturing unit 124 captures images of near-infrared light reflected from each eye using the right eye camera 116 and left eye camera 117. The image capturing unit 124 transfers the captured images to the first communication unit 118 or to the image processing unit 123.

As shown in FIG. 4, the gaze detection device 200 contains the second communication unit 220, the first gaze detection unit 221, the second gaze detection unit 222, the tracking unit 223, the image output unit 224, and the storage unit 225.

The second communication unit 220 is a communication interface having the function of communicating with the first communication unit 118 of the head mounted display 100. As mentioned above, the second communication unit 220 communicates with the first communication unit 118 using either wired or wireless communication.

The first gaze detection unit 221 receives from the second communication unit 220 the image data for gaze detection of the right eye of the user, and determines the gaze direction of the right eye of the user. Using a technique described later, the first eye-gaze detection unit 221 calculates the gaze direction vector representing the gaze direction of the right eye.

The second gaze detection unit 222 receives from the second communication unit 220 the image data for gaze detection of the left eye of the user, and determines the gaze direction of the left eye of the user. Using a technique described later, the second gaze detection unit 222 calculates the gaze direction vector representing the gaze direction of the left eye.

The tracking unit 223, using the right eye gaze direction vector sent from the gaze detection unit 221, and using the left eye gaze direction vector sent from the gaze detection unit 222, determines the point (coordinate) at which the user is looking in a three-dimensional image displayed by the display unit 108 in the head mounted display 100.

The video output unit 224 generates three-dimensional video data to be displayed by the display unit 121 in the head mounted display 100, and transfers the data to the second communication unit 220. The video output unit 224 also generates and transfers to the second communication unit 220 the data for the marker image used for gaze detection calibration. The video output unit 224 stores the location of the displayed objects in the three-dimensional coordinate system as well as in the specific coordinate system of the three-dimensional output image.

The storage unit 225 is a recording medium that stores various kinds of programs and data required for the operation of the gaze detection device 200.

Next, a description of the gaze direction detection is given as an example.

Figure 5:
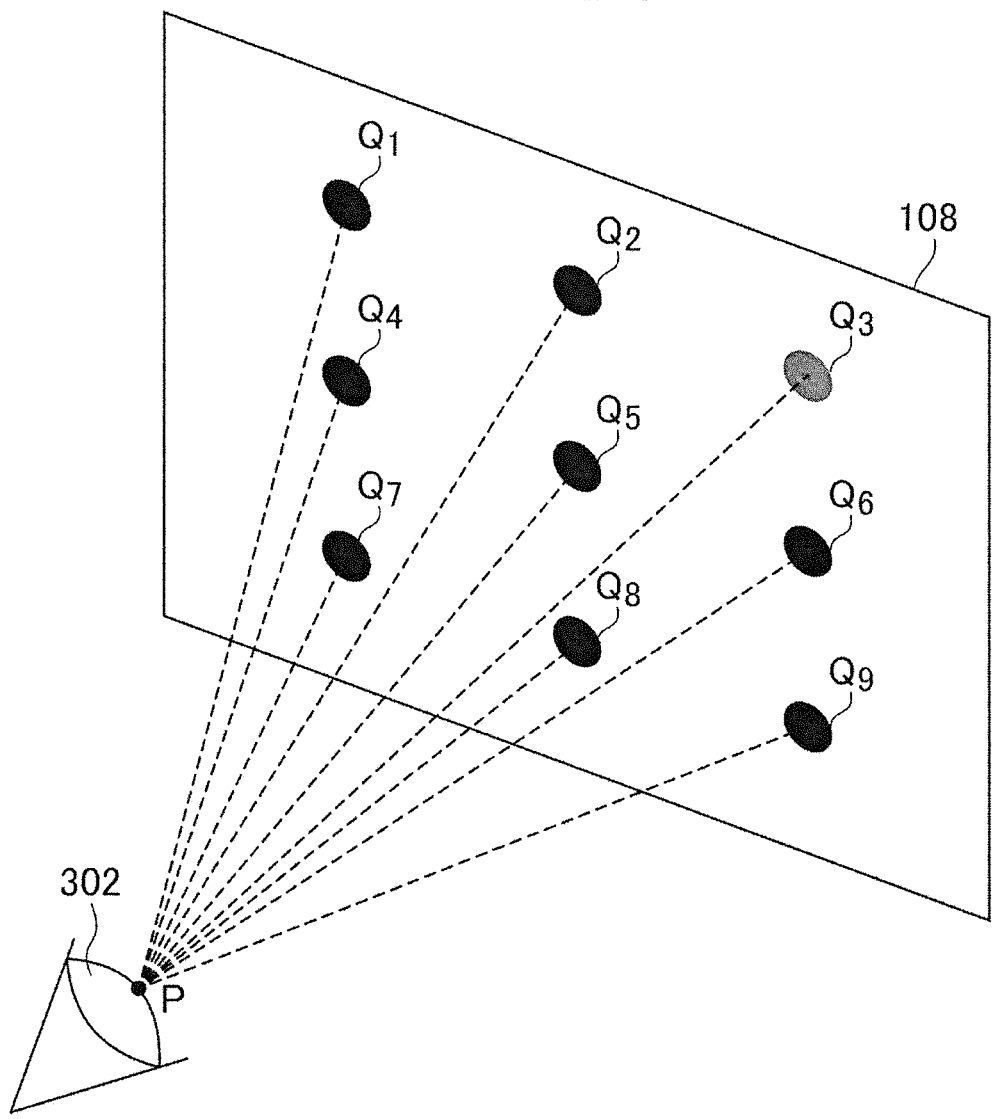
FIG. 5 is a diagram illustrating the pattern used to calibrate the gaze direction detection system.

FIG. 5 is a schematic diagram illustrating calibration of the gaze direction detection according to the example. The gaze direction of the user 300 is determined by analyzing, with the first gaze detection unit 221 and the second gaze detection unit 222 in the gaze detection device 200, the image captured by the camera 116 and transferred to the gaze detection device 200 by the first communication unit 118. Only operation of the first gaze detection unit 221 is described here, but operation of the second gaze detection unit 222 is identical.

As shown in FIG. 5, the video output unit 224 outputs nine points, $Q_1$ to $Q_9$, (marker image) that are displayed by the image display element 108 of the head mounted display 100. The gaze detection device 200 instructs the user 300 to look at the points Q1 up to Q9 sequentially. At this time, the user 300 is requested to look at each of the points without moving the neck and, to the extent possible, only moving the eyeballs. The camera 116 captures images containing the cornea 302 of the user 300 while the gaze of the user 300 is pointing at each of the nine points from $Q_1$ to $Q_9$.

Figure 6:
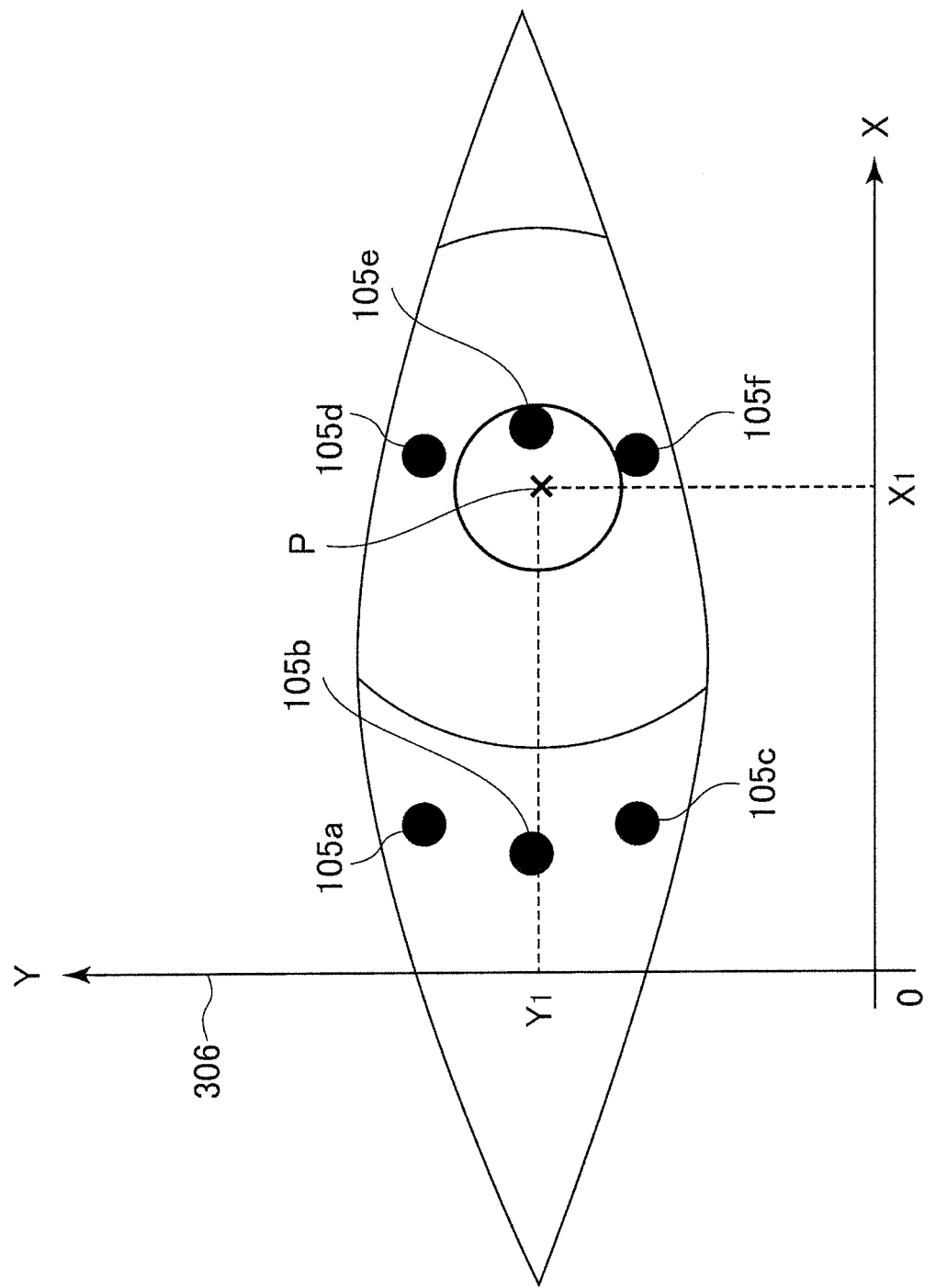
FIG. 6 is a schematic diagram illustrating the coordinate system of the user's cornea position.

FIG. 6 is a schematic diagram illustrating the position coordinates of the cornea 302 of the user 300. The first gaze detection unit 221 contained in the gaze detection device 200 analyzes the images captured by the camera 116, and detects bright spots 105 of the infrared light. While the user 300 looks at the points by turning the eyeballs only, the positions of the bright spots 105 are considered to be stationary while the user's gaze is directed at any single points. Thus, on the basis of the detected bright spots 105, the first gaze detection unit 221 sets a two-dimensional coordinate system 306 in the image captured by the camera 116.

Further, the first gaze detection unit 221 detects the center P of the cornea 302 of the user 300 by analyzing the image captured by the camera 116. This is achieved by using already-known image processing techniques such as the Hough transform or edge extraction. Thereby, the gaze detection unit 221 obtains the coordinates of the center P of the cornea 302 of the user 300 in the previously-set two-dimensional coordinate system 306.

As shown in FIG. 5, the coordinates of the displayed points $Q_1$ to $Q_9$ in the two-dimensional coordinate system set for the display screen of the image display element 108 are $Q_1(x_1, y_1)^T, Q_2(x_2, y_2)^T, \ldots, Q_9(x_9, y_9)^T$. The coordinates of, for example, the center of each point, is given by the pixel numbers. The center point P of the cornea 302 of the user 300, measured while the user 300 gazes at each of the points $Q_1$ to $Q_9$ are labeled $P_1$ to $P_9$. The coordinates of the points $P_1$ to $P_9$ in the two-dimensional coordinate system 306 are at this time $P_1(X_1, Y_1)^T, P_2(X_2, Y_2)^T, \ldots, P_9(X_9, Y_9)^T$, wherein T represents a transposed vector or a matrix.

A matrix M with the size of 2×2 is now defined by equation (1):

$$M = \begin{pmatrix} m_{11} & m_{12} \\ m_{21} & m_{22} \end{pmatrix} \qquad (1)$$

If the matrix M then satisfies equation (2), the matrix M becomes a matrix for projecting the gaze direction of the user 300 to the image plane of the image display element 108:

$$Q_N = M P_N (N=1, \ldots, 9) \qquad (2).$$

If the aforementioned equation (2) is expanded, equation (3) is obtained:

$$\begin{pmatrix} x_1 & x_2 & \ldots & x_9 \\ y_1 & y_2 & \ldots & y_9 \end{pmatrix} = \begin{pmatrix} m_{11} & m_{12} \\ m_{21} & m_{22} \end{pmatrix} \begin{pmatrix} X_1 & X_2 & \ldots & X_9 \\ Y_1 & Y_2 & \ldots & Y_9 \end{pmatrix}. \qquad (3)$$

Equation (4) is obtained by rearranging equation (3):

$$\begin{pmatrix} x_1 \\ x_2 \\ \vdots \\ x_9 \\ y_1 \\ y_2 \\ \vdots \\ y_9 \end{pmatrix} = \begin{pmatrix} X_1 & Y_1 & 0 & 0 \\ X_2 & Y_2 & 0 & 0 \\ \vdots & \vdots & \vdots & \vdots \\ X_9 & Y_9 & 0 & 0 \\ 0 & 0 & X_1 & Y_1 \\ 0 & 0 & X_2 & Y_2 \\ \vdots & \vdots & \vdots & \vdots \\ 0 & 0 & X_9 & Y_9 \end{pmatrix} \begin{pmatrix} m_{11} \\ m_{12} \\ m_{21} \\ m_{22} \end{pmatrix} \qquad (4)$$

If y, A, and x are defined as $$y = \begin{pmatrix} x_1 \\ x_2 \\ \vdots \\ x_9 \\ y_1 \\ y_2 \\ \vdots \\ y_9 \end{pmatrix}, A = \begin{pmatrix} X_1 & Y_1 & 0 & 0 \\ X_2 & Y_2 & 0 & 0 \\ \vdots & \vdots & \vdots & \vdots \\ X_9 & Y_9 & 0 & 0 \\ 0 & 0 & X_1 & Y_1 \\ 0 & 0 & X_2 & Y_2 \\ \vdots & \vdots & \vdots & \vdots \\ 0 & 0 & X_9 & Y_9 \end{pmatrix}, x = \begin{pmatrix} m_{11} \\ m_{12} \\ m_{21} \\ m_{22} \end{pmatrix}$$

equation (5) is obtained:

$$y = Ax \quad (5).$$

In equation (5), the elements of the vector y are already known because these are the coordinates of the points Q1 to Q9 displayed by the first gaze detection unit 221 on the image display element 108. Further, the elements of the matrix A are the coordinates of the vertex P of the cornea 302 of the user 300 and can be measured. Thus, the first gaze detection unit 221 can determine the vector y and the matrix A. The vector x that is the vector in which the elements of the conversion matrix M are arranged is still unknown. Since the vector y and matrix A are known, the problem of estimating the value of matrix M becomes a problem of calculating the as yet unknown vector x.

Equation (5) is an overdetermined problem if the number of equations (that is, the number of points Q presented to the user 300 during calibration by the first gaze detection unit 221) is larger than the number of the unknowns (that is, the four elements of the vector x). Since the number of equations is nine in the example shown in equation (5), it is an overdetermined problem.

An error vector between the vector y and the vector Ax is defined as vector e. That is, e=y−Ax. An optimal vector $x_{opt}$ in the sense of minimizing the sum of squares of the elements of the vector e can be calculated from equation (6):

$$x_{opt} = (A^T A)^{-1} A^T y \quad (6).$$

"−1" represents matrix inversion.

The first gaze detection unit 221 uses the elements of the calculated vector $x_{opt}$ to compose the matrix M of equation (1). Accordingly, using the coordinates of the vertex P of the cornea 302 of the user 300 and the matrix M, the first gaze detection unit 221 estimates, using equation (2), the point at which the right eye of the user 300 gazes within the two-dimensional range of the video image displayed on the image display element 108. Thereby, it becomes possible for the first gaze detection unit 221 to calculate the gaze vector linking the gaze point of the right eye on the image display element 108 and the vertex of the cornea of the right eye of the user. Similarly, the second gaze detection unit 222 can calculate the gaze vector for the left eye, connecting the gaze point of the left eye on the image display element 108 and the vertex of the cornea of the left eye of the user.

Figure 7:
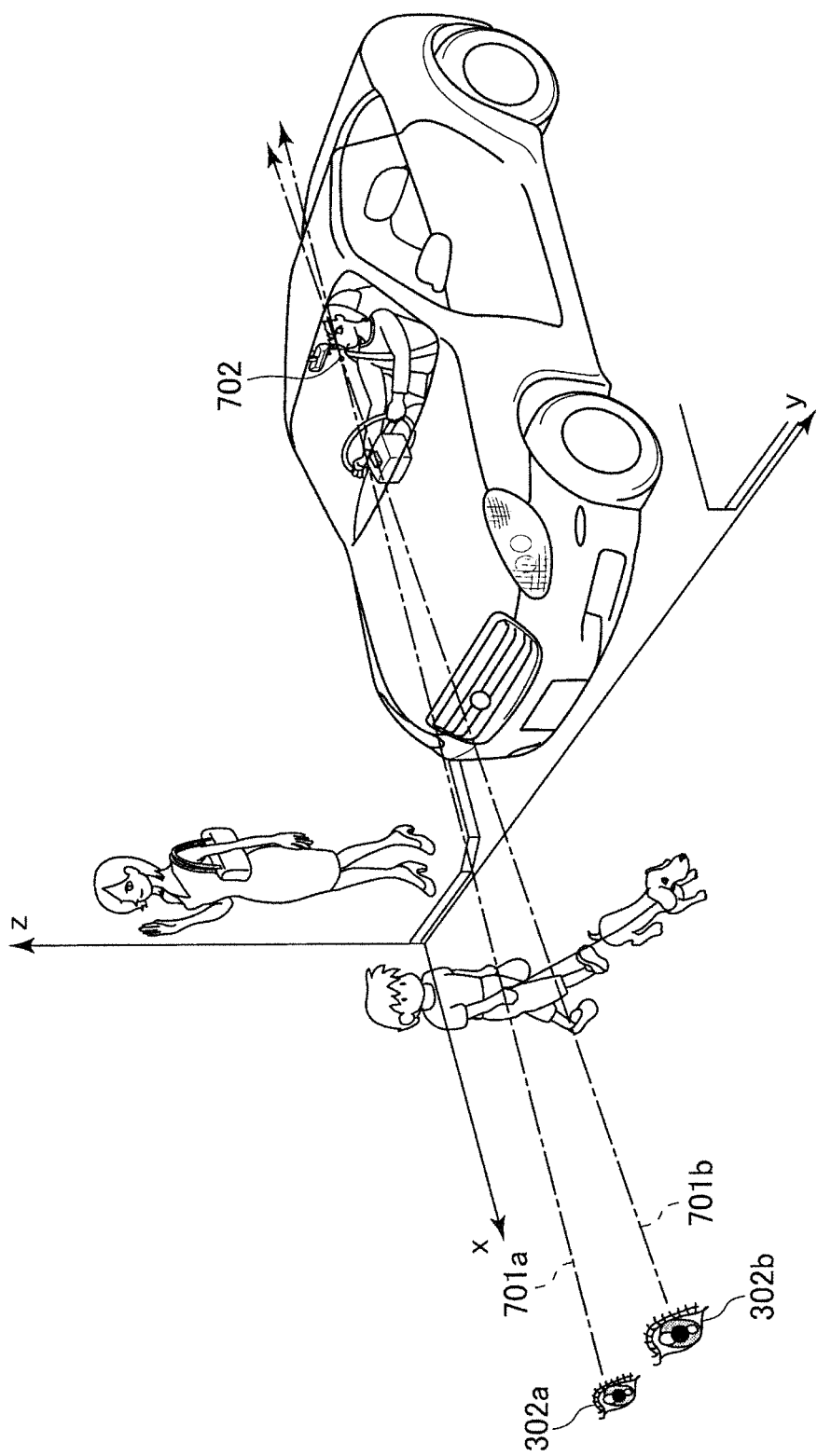
FIG. 7 is a schematic diagram of how the gaze point of a user is identified according to a first example.

FIG. 7 is a schematic diagram illustrating how the gaze location is determined according to example 1. FIG. 7 is a schematic illustration of how the left eye 302a and the right eye 302b of the user 300 perceive a three-dimensional picture in the three-dimensional image displayed by the head mounted display 100. The corresponding video image is generated by the video output unit 224 and sent by the second communication unit 220 to the head mounted display 100 for display by the image display element 108 performed by the display unit 121.

As illustrated in FIG. 7, in the field of view of the user 300, the three-dimensional image shown by the head mounted display 100 contains a boy, a dog, a woman, a passenger car, and the driver in the car. For descriptive purposes, to show clearly that this is a three-dimensional image, the three axes, the x-axis, the y-axis, and the z-axis, are shown in FIG. 7, although these axes are not necessarily shown in the image.

FIG. 7 shows that the right eye gaze vector 701a, determined on the basis of the gaze direction of the left eye 302a of the user 300, and the left eye gaze vector 701b, determined on the basis of the gaze direction of the right eye 302b of the user 300, cross at the intersection point 702. The intersection point 702 is therefore the user's focus point and will be referred to as the point at which the user gazes in the three-dimensional image. When the intersection point is obtained from the calculated gaze vectors of both eyes, it is possible to determine that the focus point is on the car driver in the background, even if there another object (a boy) is displayed in the foreground looking from the point of view of the user.

Figure 8:
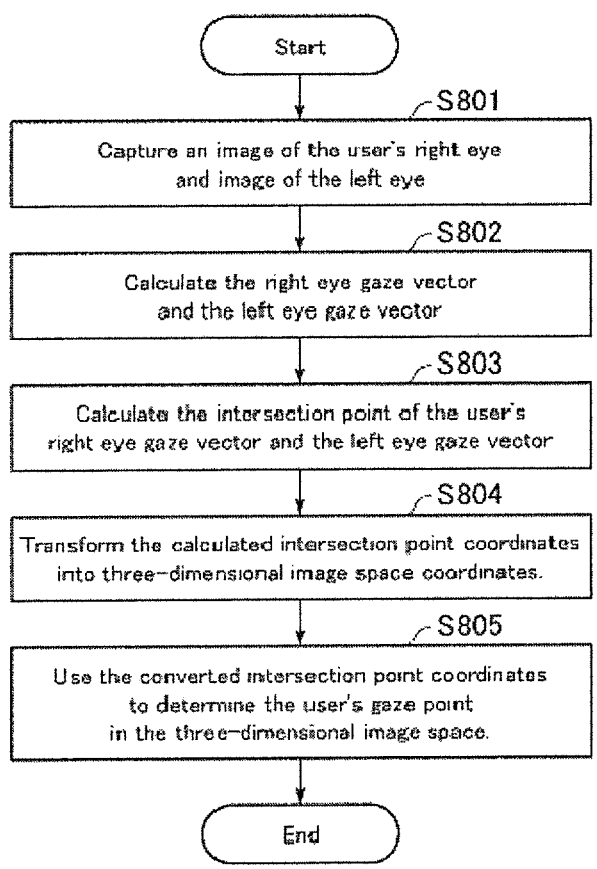
FIG. 8 is a flowchart describing operation of the head mounted display system according to the first example.

Operation of the gaze detection system 1 is explained with the help of a flowchart in FIG. 8. FIG. 8 is a flowchart explaining the operation of the gaze detection system 1.

The cameras 116 of the head mounted display 100 take images of the right eye including the infrared light reflected by the right eye, and the left eye including the infrared light reflected by the left eye (Step S801). The image capturing unit 124 transfers the right eye image and the left eye image acquired by the cameras 116 to the image processing unit 123. The image processing unit 123 performs predefined processing on the transferred image data, and delivers the processed data to the first communication unit 118. The first communication unit 118 then transmits the processed image data received from the image process unit 123 to the gaze detection device 200.

The second communication unit 210 of the gaze detection device 200 receives the image data and transfers the right eye image to the first detection unit 221 and the left eye image to the second detection unit 222.

The first gaze detection unit 221 refers the transferred right eye image and, using the above formulas, determines the gaze point of the right eye on the image display element 108. The gaze vector of the right eye is then calculated by combining the gaze point coordinates with the vertex P of the cornea of the right eye (step S802). The first gaze detection unit 221 transfers the calculated right eye gaze vector to the tracking unit 223.

The second gaze detection unit 222 refers the transferred left eye image and, using the above formulas, determines the gaze point of the left eye on the image display element 108. The gaze vector of the left eye is then calculated by combining the gaze point coordinates with the vertex P of the cornea of the left eye (Step S802). The second gaze detection unit 222 transfers the calculated left eye gaze vector to the tracking unit 223.

The tracking unit 223 computes the intersection point between the transferred right eye gaze vector and the transmitted left eye gaze vector (Step S803).

The tracking unit 223 transforms the computed intersection point to the coordinate system of the three-dimensional space of the three-dimensional image generated by the video output unit 224 (Step S804).

The tracking unit 223 determines from the transformed intersection point coordinates the location where the user is looking in the three-dimensional image space. (Step S805).

The processing illustrated in FIG. 8 is performed serially, with the gaze detection system 1 identifying the user's gaze location as necessary.

According to the example, the gaze detection system 1 can obtain both, the user's right eye gaze direction and the left eye gaze direction. Since the intersection point can be determined in the depth direction of the three-dimensional image as well, it is possible to identify the object that the user is gazing at even if there are various superimposed objects in the three-dimensional image.

Second Example

In the first example described above, the location where the user 300 is gazing in the head mounted display 100 was determined from the intersection point of the right eye gaze vector, corresponding to the gaze direction of the right eye, and the left eye gaze vector, corresponding to the gaze direction of the left eye, of the user 300.

However, right eye gaze vector computed by the first gaze detection unit 221 and the left eye gaze vector computed by the second gaze detection unit 222 do not necessarily intersect.

Thus, in this example, a method is described to identify the approximate location of the user's gaze point even when the right eye gaze vector and the left eye gaze vector have no intersection point.

In the second example, only the identification method in the tracking unit 223 is different, the other parts are common with the first example and, therefore, except for the tracking unit 223, detailed explanations are omitted.

In the second example, a three-dimensional image is displayed in multiple layers. In the second example of the tracking unit 223, the user's gaze location (layer) is identified by calculating the distance between the intersection point of the user's right eye gaze vector with a layer and the intersection point of the left eye gaze vector with the same layer and finding the layer with the shortest distance between the intersection points. To explain in more detail, the interaction points of the right eye gaze vector with layers L1, L2, L3, . . . , are Pr1, Pr2, Pr3, . . . , and the intersection points of the left eye gaze vector with the layers L1, L2, L3, . . . are Pl1, Pl2, Pl3, . . . . The distances between the intersection points Pr1 and Pl1 is D1, the distance between Pr2 and Pl2 is D2, the distance between Pr3 and Pl3 is D3, . . . . The tracking unit 223 finds the shortest distance among calculated intersection point distances D1, D2, D3, . . . . The user's eye gaze location (layer) is thus determined by selecting a layer for which the distance between the intersection points is the smallest.

Figure 9:
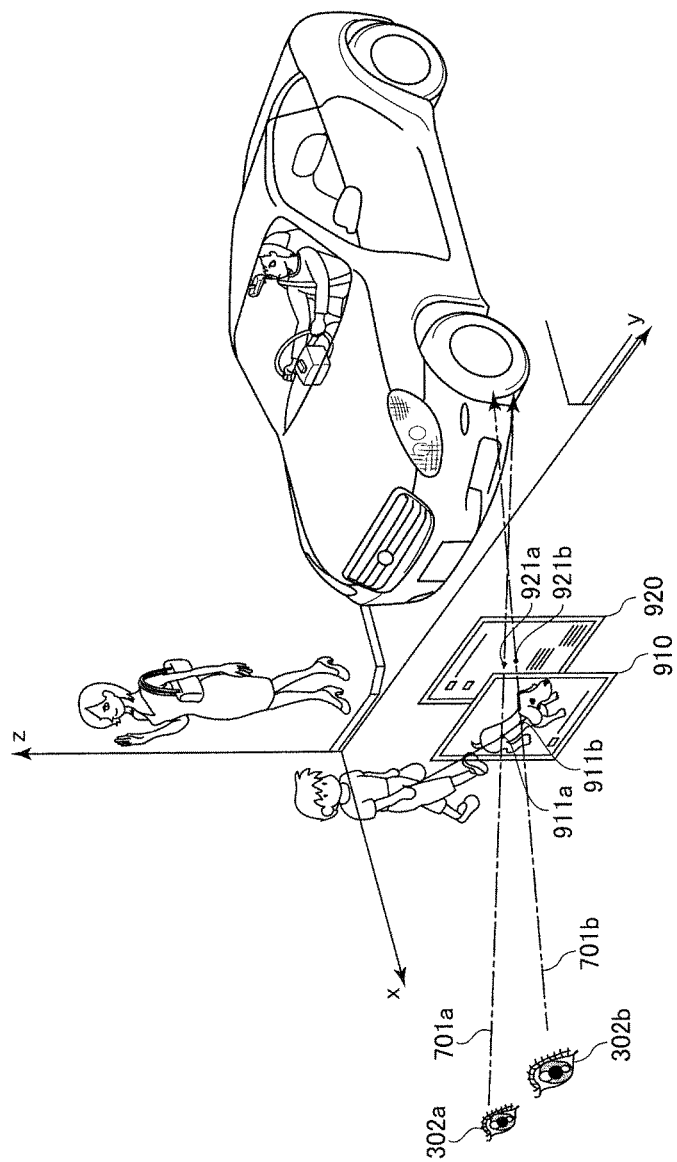
FIG. 9 is a schematic illustration of how the gaze point of a user is identified according to a second example.

FIG. 9 illustrates schematically the method of determining the gaze location according to the second example. In this example, it is assumed that an image similar to the picture in FIG. 9 is displayed in the head mounted display 100. The different point from example 1 is that in the three-dimensional image, several kinds of information are shown in a menu image 910 or a menu image 920 that are displayed in the three-dimensional image. These menu images 910, 920 are displayed in the three-dimensional image that is structured in a plurality of layers. This image is generated by the video output unit 224, transferred to the second communication unit 220, and sent to the head mounted display 100, where the image is displayed by the display unit 121 on the image display element 108.

In the second example, an example is given where identifying the menu image (layer) that the user is gazing at is based on the intersection points where the left eye gaze vector 701*a* and the right eye gaze vector 701*b* of the user 300 intersect with the menu images 910, 920.

As shown more precisely in FIG. 9, the intersection point 911*a* is defined by the intersection of the right eye gaze vector 701*a* of the user 300 and the menu image 910. Also, the intersection point 911*b* is defined by the intersection of the left eye gaze vector 701*b* of the user 300 and the menu image 910. The distance between the intersection point 911*a* and the intersection point 911*b* is D1.

On the other hand, as shown in FIG. 9, the intersection point 921*a* is defined by the intersection of the right eye gaze vector 701*a* of the user 300 and the menu image 920. Also, the intersection point 921*b* is defined by the intersection of the left eye gaze vector 701*b* of the user 300 and the menu image 920. The distance between the intersection point 921*a* and the intersection point 921*b* is D2.

Among the distances D1 and D2 calculated in this way, the shorter distance defines the location (layer) where the gaze of the user 300 is pointing at.

Figure 10:
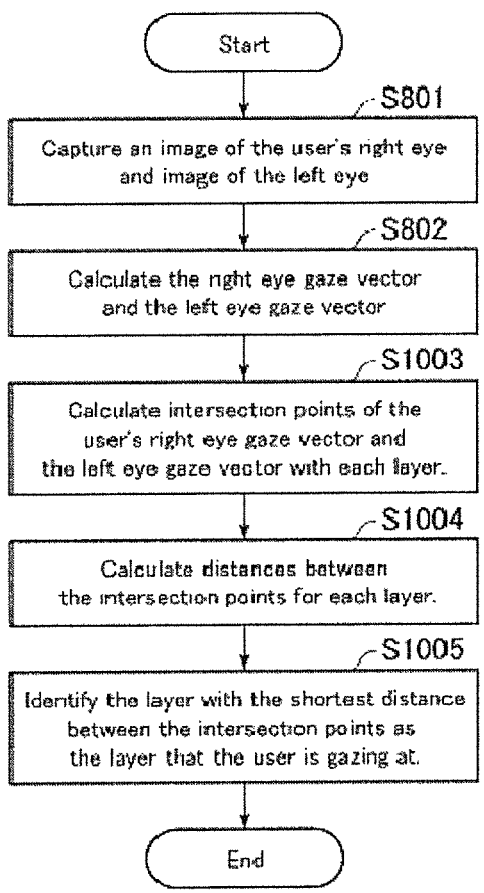
FIG. 10 is a flowchart describing operation of the head mounted display system according to the second example.

FIG. 10 shows a flowchart describing operation of the gaze detection system 1 according to the second example. This flowchart is identical to the first example up to the step S802 and explanation of the operation up to that step is omitted.

The user's right eye gaze vector and the left eye gaze vector sent to the tracking unit 223 are used to calculate the intersection points with each layer among the layers displayed in the three-dimensional image (Step S1003). That is, in the example in FIG. 9, the tracking unit 223 calculates the intersection points for the menu image 910 and for the menu image 920.

The tracking unit 223 calculates the intersection point distances between the right eye gaze vector intersection point and the left eye gaze vector intersection point for each layer (Step S1004).

The tracking unit 223 finds the shortest distance among the distances between the calculated intersection points. The user's gaze location (layer) is then determined by selecting the layer for which the distance between the intersection points is the shortest. (Step S1005).

In the second example, an example of determining the gaze point is considered where a menu or other image data is displayed in a layered structure as shown in FIG. 9, the three-dimensional image layers may be a plurality of layers stacked along the x-axis direction (depth direction).

For example, when virtual planar layers, parallel to the y-z plane, are present at x-axis coordinates x1, x2, x3, the above method can be used to identify the layer that the user 300 is gazing as the virtual layer having the shortest distance between the intersection points.

According to the second example, the method used in the gaze detection system 1 to determine the place where a user is gazing in a three-dimensional image is effective when the calculated right eye gaze vector and the left eye gaze vector do not have an intersection point. Also, when a three-dimensional image is considered to consist of a plurality of layers, it becomes easy to determine the user's gaze location by calculating the intersection point distances.

Third Example

In the second example, the three-dimensional image was made up of a plurality of layers and the intersection points of the gaze vector of the user 300 with each layer were used to find the layer for which the distance between the intersection points was the shortest, allowing the layer that the user was gazing at to be determined.

In the third example, a method of determining the user's gaze point is disclosed for when the three-dimensional 3D image does not have a layered structure and the right eye gaze vector and the left eye gaze vector do not intersect.

In the third example, only the detection method in the tracking unit 223 is different, while other functions are the same as in the first example and second examples, and detailed explanation is omitted except for the tracking unit 223.

The difference in the operation of the tracking unit 223 from examples 1 and 2 is that a cylinder with a given radius is centered on the left eye gaze vector 701*a*, and another cylinder with a given radius is centered on the right eye gaze vector 701*b*, and an object in the three-dimensional image that is closest to the intersection region of the cylinders is identified as the point that the user is gazing at.

Figure 11:
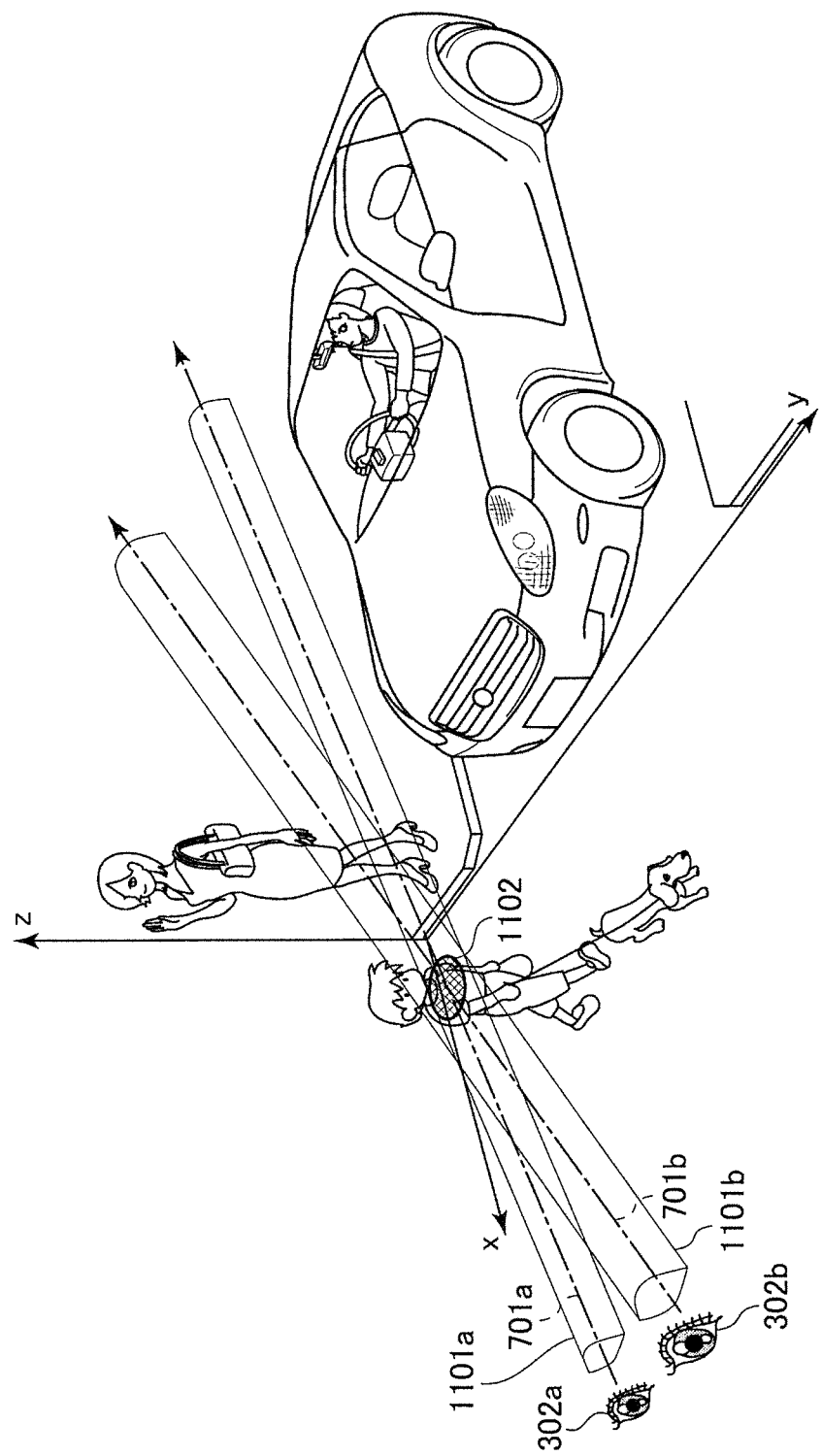
FIG. 11 is a schematic illustration of how the gaze point of a user is identified according to a third example.

FIG. 11 is a schematic illustration of how the gaze location of the user 300 is determined in example 3. The relevant image is generated by the video output unit 224, sent to the head mounted display 100 by the second communication unit 220, and displayed on the image display element 108 by the display unit 121. As shown in FIG. 11, a cylinder 1101a with a given radius is assumed to be centered on the user's left eye gaze vector 701a. In the same way, a cylinder 1101b with a given radius is assumed to be centered on the user's right eye gaze vector. The region 1102, where the cylinder 1101a and the cylinder 1101b intersect, is identified as the place where the user 300 is gazing. Thus, the user 300 is gazing at the boy in the three-dimensional image.

Figure 12:
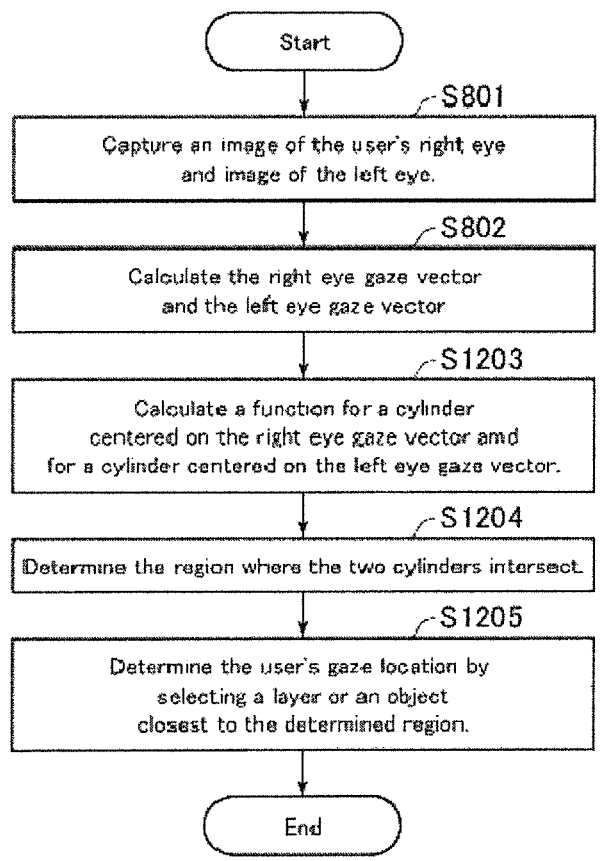
FIG. 12 is a flowchart describing operation of the head mounted display system according to the third example.

FIG. 12 is a flowchart describing the operation of the gaze detection system 1 according to the third example. The flowchart up to the step S801 is common with the first example, and explanation up to that point is omitted.

The left eye gaze vector and the right eye gaze vector are transferred to the tracking unit 223, which uses formula F to calculate the cylinder 1101a centered on the left eye gaze vector. Also, the tracking unit 223 uses formula G to calculate the cylinder 1101b, centered on the right eye gaze vector (step S1203).

Based on formula F and formula G, the tracking unit 223 determines the area 1102 where the cylinder 1101a and the cylinder 1101b intersect (step S1203).

The tracking unit 223 then finds a layer or an object that is closest to the determined area and identifies that object as the place where the user is gazing at.

In example 3, the functions of the two abovementioned cylinders need to be evaluated, increasing the computational complexity of the intersection region calculation, causing the processing load of the gaze detection device 200 to become large. Therefore, to reduce the number of required operation, the following method may be used.

The tracking unit 223 calculates a plurality of right eye parallel vectors that are parallel to the right eye gaze vector and centered on the right eye gaze vector. In the same way, the tracking unit 223 calculates a plurality of left eye parallel vectors that are parallel to the left eye gaze vector and centered on the right eye gaze vector. Intersection points are then calculated for each right eye parallel vector with each left eye parallel vector. The tracking unit 223 calculates the center point of the plurality of obtained intersection points. The tracking unit 223 defines the three-dimensional image coordinates corresponding to the calculated center point as the gaze location of the user 300.

According to the third example, it is possible to determine the gaze location of the user 300 even if the user's left eye gaze vector 701a and the right eye gaze vector 701b have no intersection point and the three-dimensional image does not have a layered structure.

Our gaze detection system is not limited to examples 1 to 3, it is clear that other approaches to realize the spirit of our systems and methods can be used.

For example, although the third example described how to detect the intersection region of two cylinders, other than cylinder shapes, for example, rectangular column shapes, can be used for the calculation as well. The use of a square column instead of a cylinder simplifies the calculation.

In the above examples, although a technique to detect the gaze of the user 300 by acquiring an image of an eye reflected from the hot mirror 112 was described, the mirror can be omitted and the eye of the user 300 may be imaged directly.

In the aforementioned examples, the processor of the gaze detection device 200 executes a gaze detection or other programs and determines the point at which the user gazes. The gaze detection device 200 may be implemented as an IC (integrated circuit), LSI (Large-Scale integration), or other dedicated logic circuit. The implementation may consist of one or more circuits, and the functions of a plurality of functional units shown in the aforementioned example may be implemented in a single integrated circuit. Depending on the degree of integration, the LSI may be referred to as VLSI, super LSI, ultra LSI or the like.

The gaze detection program may be recorded on a recording medium that is readable by a processor. A "non-transitory tangible medium" such as a tape, a disc, a card, a semiconductor memory, a programmable logic circuit or the like is used as the recording medium.

The aforementioned search program may be provided to the aforementioned processor through any transmission medium (such as communication network, wireless link or the like) that can transmit the search program. The abovementioned gaze detection program may be achieved in the forms of data signals embedded in transmission wave, or it may be implemented in the form of embedded data signal of a carrier wave.

The aforementioned gaze detection program may be implemented by using, for example, a script language such as ActionScript or JavaScript (registered trademark), an object-oriented language such as Objective-C or Java (registered trademark), or a markup language such as HTML5.

What is claimed is:

1. A gaze detection system comprising:
    a head mounted display, mounted on a user's head for use, comprising,
        a first infrared light source unit illuminating a user's right eye with infrared light;
        a second infrared light source unit illuminating a user's left eye with infrared light;
        a first image capturing device imaging the right eye illuminated by the infrared light;
        a second image capturing device imaging the left eye illuminated by the infrared light; and
        a display unit displaying a three-dimensional image, and
    a gaze detection device detecting a gaze of the user comprising,
        a first detection unit detecting a gaze direction of the right eye based on the image captured by the first image capturing device;
        a second detection unit detecting a gaze direction of the left eye based on the image captured by the second image capturing device; and
        a tracking unit that determines a gaze point of the user in the three-dimensional image on the basis of the gaze direction of the right eye and the gaze direction of the left eye,
        in which the first detection unit calculates the right eye gaze vector indicating the gaze direction of the right eye, and the second detection unit calculates the left eye gaze vector indicating the gaze direction of the left eye,
    wherein the display unit displays a three-dimensional image consisting of a plurality of layers in a depth direction, and the tracking unit identifies the layer that the user is gazing at by selecting the layer having a shortest distance between intersection points of the right eye gaze vector and the left eye gaze vector with each layer.

2. The gaze detection system of claim 1, wherein the tracking unit identifies the user's gaze location based on the intersection point between the right eye gaze vector and the left eye gaze vector.

3. The gaze detection system of claim 1, wherein the tracking unit identifies the user's gaze location based on the intersection region of a cylinder with a given radius, centered on the right eye gaze vector and a cylinder with a given radius, centered on the right eye gaze vector.

4. The gaze detection system according to claim 1, wherein the tracking unit identifies the gaze location of the user based on the intersection points of the first plurality of parallel vectors parallel to the right eye gaze vector and the second plurality of parallel vectors parallel to the left eye gaze vector.

5. A method of determining a gaze point of a user in a gaze detection system comprising a head mounted display worn on the head of the user and a gaze detection device determining the gaze point of the user, comprising:
displaying a three-dimensional image on the head mounted display;
illuminating a user's right eye and left eye with infrared light from an infrared light source;
acquiring images of the user's right eye and left eye illuminated by the infrared light;
transferring an acquired image data to the gaze detection device;
determining in the gaze detection device the user's right eye gaze direction vector showing the gaze direction of the user's right eye based on the acquired image of the right eye;
determining in the gaze detection device the user's left eye gaze direction vector showing the gaze direction of the user's left eye based on the acquired image of the left eye; and
determining a location that the user is gazing at in the three-dimensional image based on the right eye gaze direction and the left eye gaze direction,
in which the head mounted display displays a three-dimensional image consisting of a plurality of layers in the depth direction, wherein
the detection device identifies a layer the user is gazing at by selecting the layer having a shortest distance between the intersection points of the right eye gaze vector and the left eye gaze vector with each layer.

6. A gaze detection program executing on a computer that determines a gaze point of a user wearing a head mounted display that displays a three-dimensional image, wherein the computer comprises:
a function of obtaining the image data, acquired under infrared light illumination, of a right eye and a left eye of the user wearing the head mounted display;
a function of detecting a right eye gaze direction of the right eye based on the image data of the right eye;
a function of detecting a left eye gaze direction of the left eye based on the image data of the left eye;
a function of determining a gaze point of the user in the three-dimensional image based on the right eye gaze direction and the left eye gaze direction;
a function of calculating a right eye gaze vector indicating the gaze direction of the right eye;
a function of calculating a left eye gaze vector indicating the gaze direction of the left eye; and
a function of displaying a three-dimensional image consisting of a plurality of layers in a depth direction, wherein
the function of detecting the gaze direction identifies the layer that the user is gazing at by selecting the layer having a shortest distance between intersection points of the right eye gaze vector and the left eye gaze vector with each layer.

* * * * *